(12) United States Patent
Urizar Ursua et al.

(10) Patent No.: US 12,345,956 B2
(45) Date of Patent: Jul. 1, 2025

(54) APPARATUS AND METHOD FOR PROJECTING A PAL LENS IN FRONT OF AN EYE

(71) Applicant: 2EYES VISION, S.L., Madrid (ES)

(72) Inventors: María Pilar Urizar Ursua, Madrid (ES); Enrique Gambra Urralburu, Madrid (ES); Carlos Dorronsoro Diaz, Madrid (ES)

(73) Assignee: 2EYES VISION, S.L., Madrid (ES)

( * ) Notice: Subject to any disclaimer, the term of this patent is extended or adjusted under 35 U.S.C. 154(b) by 0 days.

(21) Appl. No.: 18/843,416

(22) PCT Filed: Feb. 28, 2023

(86) PCT No.: PCT/EP2023/055053
§ 371 (c)(1),
(2) Date: Sep. 3, 2024

(87) PCT Pub. No.: WO2023/165998
PCT Pub. Date: Sep. 7, 2023

(65) Prior Publication Data
US 2025/0110356 A1     Apr. 3, 2025

(30) Foreign Application Priority Data

Mar. 1, 2022   (EP) ..................... 22382175

(51) Int. Cl.
*G02C 13/00* (2006.01)
*A61B 3/04* (2006.01)
(Continued)

(52) U.S. Cl.
CPC .............. *G02C 13/003* (2013.01); *A61B 3/04* (2013.01); *G02C 7/028* (2013.01)

(58) Field of Classification Search
CPC .......... G02C 13/003; G02C 7/028; A61B 3/04
See application file for complete search history.

(56) References Cited

U.S. PATENT DOCUMENTS 3,945,713 A    3/1976  Doi
8,169,538 B2 *  5/2012  Miura .................. G02B 17/026
                                         348/337

(Continued)

FOREIGN PATENT DOCUMENTS

ES       2346175 A1    10/2010
JP       H05277070 A   10/1993

OTHER PUBLICATIONS

International Search Report for related patent application PCT/EP2023/055053 prepared by the European Patent Office and dated Jun. 15, 2023, in English.

(Continued)

*Primary Examiner* — Tuyen Tra
(74) *Attorney, Agent, or Firm* — Snell & Wilmer LLP (57) ABSTRACT

An apparatus for projecting a progressive addition lens in front of an eye of a user of the apparatus includes a first support for supporting the progressive addition lens in a PAL plane; a projection system configured for projecting without inversion the PAL plane onto a conjugated PAL plane, and generating a non-inverted projection of an object through the PAL plane onto a retina of the eye; wherein in the position of use of the apparatus the first support is configured to support the PAL lens such that the PAL plane is placed in a distal portion of the apparatus; the projection system is located between the PAL plane and the eye; a proximal portion of the apparatus is to be placed in front of the eye, and the eye is placed at a first distance from the conjugated PAL plane.

17 Claims, 10 Drawing Sheets

(51) Int. Cl.
    *G02C 7/02*        (2006.01)
    *G02C 7/04*        (2006.01)

(56) References Cited

U.S. PATENT DOCUMENTS

| | | |
|---|---|---|
| 8,857,990 B2 | 10/2014 | Spivey |
| D842,449 S | 3/2019 | Chang et al. |
| 2013/0025045 A1 | 1/2013 | Gagnon |
| 2017/0108702 A1* | 4/2017 | Rabner .................. G02B 30/35 |

OTHER PUBLICATIONS

Written Opinion by the International Searching Authority for related patent application PCT/EP2023/055053 prepared by the European Patent Office and dated Jun. 15, 2023, in English.

\* cited by examiner

APPARATUS AND METHOD FOR PROJECTING A PAL LENS IN FRONT OF AN EYE

TECHNICAL FIELD

The present invention relates to the field of visual optics, ophthalmology and optometry and has application in the prescription of ophthalmic progressive lenses (progressive spectacle glasses).

STATE OF THE ART

Presbyopia is the loss of the accommodation ability of the eye that occurs due to aging, affecting an estimation of 1.7 billion people worldwide. This accommodation ability is related to the change of optical power, or focal length, by the crystalline lens between near and far distance vision. Whereas until the age of 20 this accommodation ability remains relatively stable, the loss in accommodation ability becomes more noticeable around the age of 50, when it tends to a continuous loss with aging due to stiffening of the crystalline lens. This loss of accommodation prevents the eye from being able to focus objects at near and intermediate distances, making it difficult to carry out common tasks such as reading.

There are essentially three solutions for presbyopia correction: the use of ophthalmic lenses, the use of multifocal contact lenses and the implantation of intraocular lenses (IOL) which implies undergoing surgery. The preferred solution is the use of ophthalmic lenses, due to their quality and their non-invasive aspect.

These ophthalmic lenses can be of three types: monofocal, which enable the user to see only at a near distance; bifocal, enabling the user to see at two different distances; and progressive (progressive addition lenses, in the following also referred to as "PAL" or "PAL lens(es)), which allow the user to see through a wide range of distances from far to near through the same lens. In view of the comfort and functionality, progressive ophthalmic lenses are usually considered the most beneficial solution.

Figure 1A:
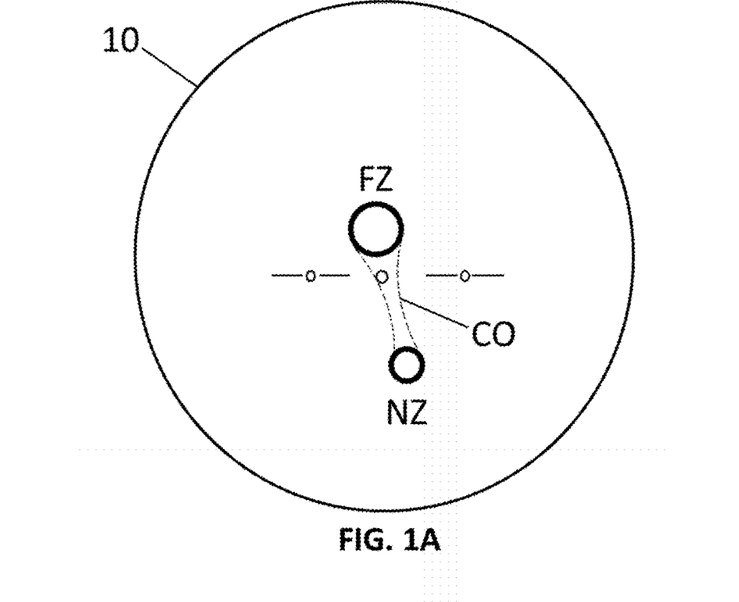
FIG. 1A schematically shows a blank PAL lens and its far and near zones FZ, NZ and the corridor CO between both zones.

Progressive addition lenses are optical elements with variable optical power through its surface, allowing the user to have good vision at different distances with the same PAL lens. FIG. 1A shows a schematic representation of a blank PAL lens 10 where the top and bottom zones of the PAL lens 10 are dedicated to far vision and near vision, respectively; these far vision zone FZ and near vision zone NZ are vertically separated, the progressive region between both zones being named the corridor CO.

Figure 1B:
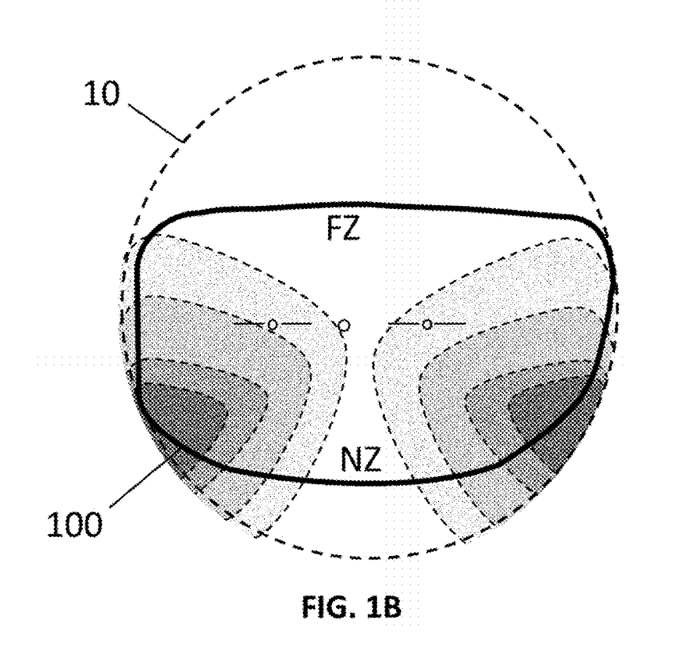
FIG. 1B schematically represents the optical performance of a PAL lens, showing the lateral aberrations generated by the PAL lens.

As shown in FIG. 1B, due to the existence of the corridor between the far and the near vision zones, lateral aberrations are generated at the sides of the corridor, which affect clarity of vision through the sides of the lens. These aberrations are represented by the shadowed areas; the darker the shadow, the higher the aberration degree. The degree of the aberration increases from the center of the corridor to the edge of the PAL and from the far vision zone FZ to the near vision zone NZ. Reference number 100 represents the spectacle's frame where such PAL lens would be mounted. Thus, representing the area of interest of the blank PAL lens that would be used for the final spectacle.

Figure 1C:
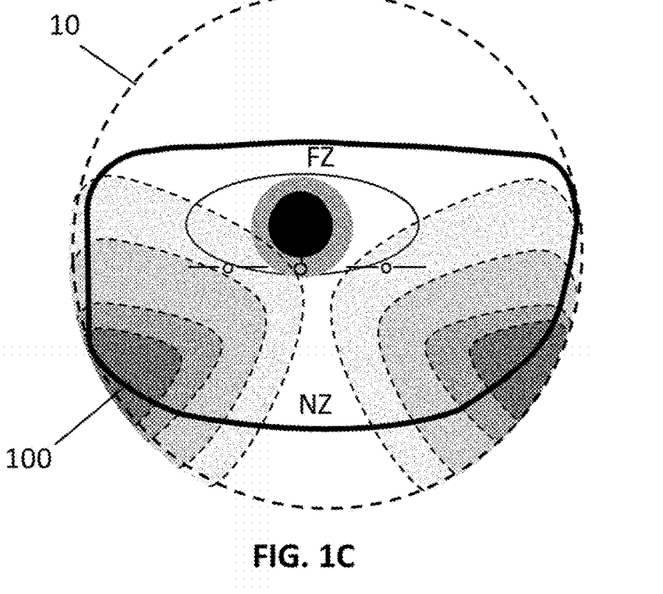
FIG. 1C schematically shows an example of an eye position of a user at the PAL when the line of sight of the user goes through the far zone FZ.
Figure 1D:
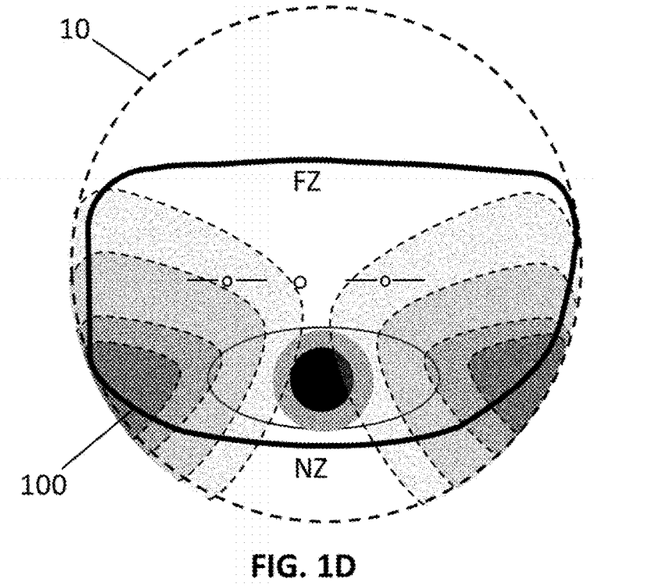
FIG. 1D schematically shows an example of an eye position of a user at the PAL when the line of sight of the user goes through the near zone NZ.

The spatial distribution of each vision zone also leads to a need of a displacement of the user's line of sight to focus on each distance vision. For the observance of objects at a far distance the user needs to see through the top area of the lens as represented in FIG. 1C, while for the observance of objects at a near distance the user needs to see through the bottom area of the lens as represented in FIG. 1D.

Figure 2A:
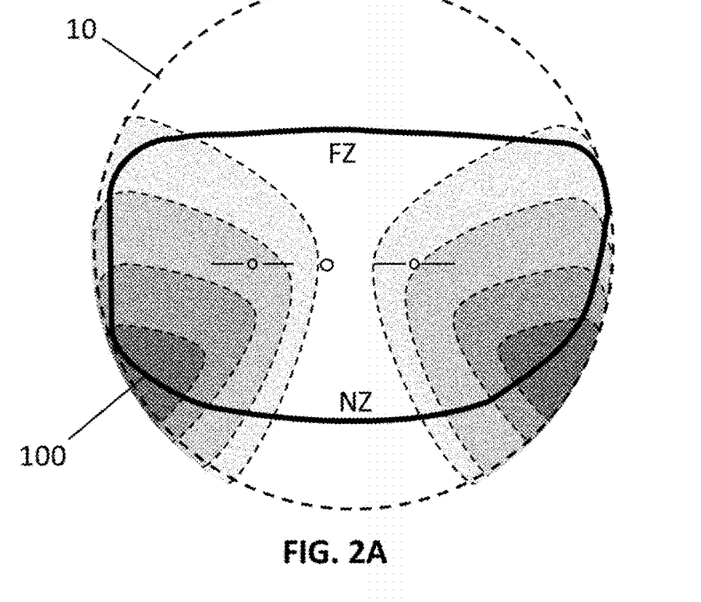
FIGS. 2A and 2B schematically show the sort of aberrations produced across the PAL when using a hard and a soft, respectively, optical design of a PAL lens. A hard design provides larger areas of sharp vision for far and near zones, but the amount of lateral aberrations (and therefore blur) is higher with respect to a soft design.
Figure 2B:
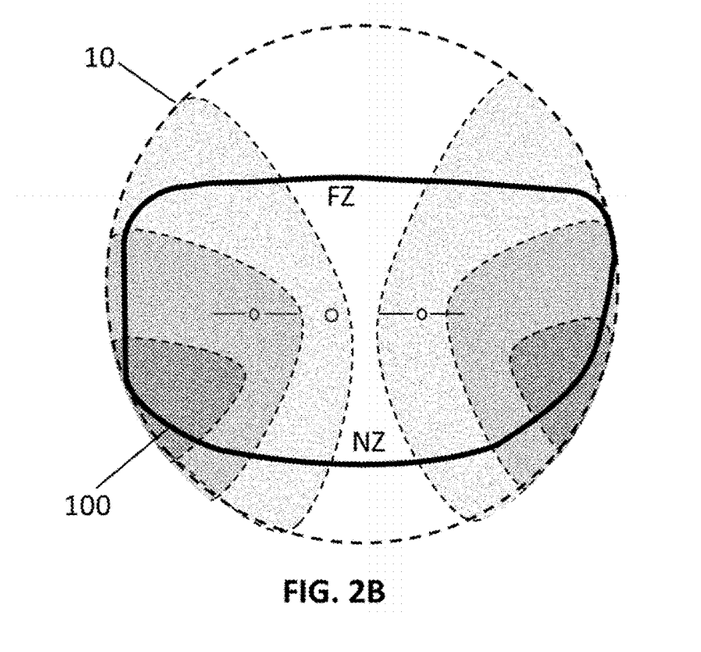

PAL lenses are lenses with a high value added in which manufacturers invert a reasonable amount of R+D effort to improve their quality and property. Technological advances in the design and the manufacturing of PALs have allowed to achieve a high level of customization. Two main categories of PAL optical designs are usually considered. And:
 when a hard design is used (which is schematically shown in FIG. 2A), sharp vision is achieved through a wider area of each vision zone, the far zone FZ and the near zone NZ, but in exchange, stronger aberration profiles are generated, and blur is higher in the sides; and
 when a soft design is used (which is schematically shown in FIG. 2B), sharp vision is achieved in a smaller area of each vision zone, but in exchange, smoother aberration profiles are present.

In any case, due to these lateral aberrations, around 5% of users of PAL lenses face significant problems with their adaptation to PALs. This implies that a significant number of PAL lenses are returned and new PAL lenses with a different design have to be manufactured. This has consequences over the whole value chain in the sale of PAL lenses, from the manufacturer to the end user, including the environment since the returned glasses—highly customized for the user and costly to manufacture—cannot be reused.

During the last years, there has been significant work in selecting the optical design of the PAL with respect to the spectacle's frames and the user facial features, as well as the head and eyes movements of the user. However, the selection of the optical design parameters with respect to the user's preference and tolerance to blur is still nowadays a challenge. Current methods include the use of questionaries and assumptions that do not necessarily lead to an optimal adaptation of the user to the optical design selected.

There has been some improvement with the appearance of lenses simulators and virtual reality systems. However, they have not proven to be completely satisfactory. A few ophthalmic lenses simulators have appeared in the market based on adaptive optical elements. Electro-tunable lenses (ETL) or deformable-mirror spatial light modulator (SLM) have been used to simulate multifocal vision, allowing user to have a realistic experience of far and near distances vision. Either desktop simulators (see, for instance, patent document US2013025045) and see-through head mount devices (see, for instance, patent document ES2346175) are based on the projection of a temporal profile of a focal length variation in the user's vision. This way, due to the advantage of a fast focal length modulation and based on temporal multiplexing principle, different temporal profiles of an adaptive optical element lead to the simulation of different optical designs of multifocal lenses. These systems have proven to represent accurately preoperatively the optical performance of commercial intraocular lenses (IOL), and in the near future will help doctor's in selecting the most appropriate IOL and therefore increase patient satisfaction providing the optimal solution and better management of expectations along the process. However, the fact that the multifocality profile is generated temporally and not with a spatial distribution through the optical surface of the simulator, prevents the use of these systems for the simulation of PALS.

Another different approach is the use of 3D virtual reality (VR) technology, which is usually based on a computer simulation of the addition and aberration profile of a PAL. In this case, the scene shown to the user is affected by a computer-generated aberration profile of and ideal PAL. But these systems present the disadvantage of having a reduced field of view; and they do not allow a realistic observation of the surrounding environment and thus, require an extrapolation from what is being observed to what the final vision through the PAL would be.

Another recent technique is augmented reality (AR). As with VR, AR is also based on a computer-generated profile of the PAL superimposed on the natural vision of the surrounding elements. The advantages of AR systems with respect to VR is that they allow a wider field of view as well as the observation of the natural environment of the user. Even so, they still do not provide a completely realistic representation of the progressive lenses as the progressive profile of the optics is computer simulated.

The fact is that with PALs designed using AR or VR systems, the user still rejects the actual PAL lens they get.

Thus, there is a need for a system that overcomes the drawbacks of the existing solutions and provides the user the possibility of experiencing vision through different designs of progressive lenses before manufacturing them, with all the optical implications, and in a real visual environment.

DESCRIPTION OF THE INVENTION

The present disclosure intends to solve the shortcomings of prior-art devices and methods by providing an apparatus and a method that are capable of projecting a PAL lens into the user's vision, giving the user a more realistic experience.

A first aspect of the present disclosure relates to an apparatus for projecting a progressive addition lens (or PAL lens) in an eye, in front thereof, of a user of the apparatus. The apparatus comprises:
  a first support for supporting the progressive addition lens in a PAL plane;
  a projection system configured for
    projecting without inversion the PAL plane onto a conjugated PAL plane;
    generating a non-inverted projection of an object through the PAL plane onto a retina of the eye.
  In the position of use of the apparatus:
  the first support is configured to support the PAL lens such that the PAL plane is placed in a distal portion of the apparatus;
  the projection system is located between the PAL plane and the eye;
  a proximal portion of the apparatus is to be placed in front of the eye, and
    the eye is placed at a first distance from the conjugated PAL plane.

That is, in the position of use of the apparatus and in the direction of light coming from an external object and going through the apparatus:
  the first support for the PAL lens is configured to place the PAL lens before the projection system, so that the PAL lens will be located at a distal portion of the apparatus;
  the projection system is located between the PAL plane and the eye; and,
  the eye is placed in front of a proximal end of the apparatus and at the first distance from the conjugated PAL plane, thus, after the conjugated PAL plane at that first distance.

When the apparatus is in use, the eye of the user is placed after the projection system at the first distance from the conjugated PAL plane. In certain embodiments, this first distance is made equal or approximately equal to the vertex distance of a spectacle lens. By configuring the apparatus so that, in its position of use, the eye is placed at around the vertex distance from the conjugated PAL plane the user can really experience the vision through the PAL lens and see the object (or objects therethrough) as if the PAL lens were mounted on an actual spectacle frame.

The object or objects to be placed in front of the apparatus can be an external object or a visual object or any other object or objects. The object or objects can be a chart or an optotype such as far or near visual charts in a clinical room; an electronic device such as TV, a cell phone; a book, a room, a window, people at different distances or any natural or artificial visual scene.

In certain embodiments, the object is placeable in front of the PAL lens, in such a way that the light coming from the object goes through the PAL, traverses the projections system PS and reaches the eye, which forms an image of the object seen through the PAL and the PS on the retina. The object is to be placed at a distance from the PAL lens, the distance typically being at least 20 cm.

The vertex distance is defined in the clinical practice as the distance between the back surface of a corrective lens, i.e. glasses (spectacles) or contact lenses, and the front surface of the cornea. For spectacles, the vertex distance is typically around 12 mm.

The apparatus just defined, which can be preferably embodied as a head-mounted apparatus, is capable of projecting a blank ophthalmic progressive lens into the user's vision. Thus, a user of the apparatus can directly observe their surrounding environment through a variety of real PAL lenses without the need to mentally extrapolate their experience from the simulation to what they would see with their progressive lenses.

With the apparatus of the present disclosure as just defined, users are thus able to learn how different progressive lenses perform before the definite spectacle glasses are actually manufactured and are capable of identifying the design option that better suits him/her or is more comfortable for the user.

In certain embodiments, the apparatus further comprises a second support for supporting at least one trial lens in a first trial lens plane, the second support being configured to support the at least one trial lens in front of the eye, at a second distance therefrom. The apparatus may further comprise a third support for supporting at least one trial lens in a second lens plane, the second lens plane being configured to be projected at a conjugated trial lens plane at the pupil of the eye or at a second distance from the eye (which second distance can be around 12 mm, and it can be in the range of 10 mm and 20 mm). Advantageously, and according to either embodiment, the apparatus can project a PAL lens into the user's vision together with their refractive error included in the trial lens (thereby including the corresponding myopia, hyperopia or astigmatism correction needed by the user), providing a more realistic experience, and allowing, at the same time, to use the same PAL lens with any user.

In this sense, the at least one trial lens to be supported by the second support and/or by the third support can have an optical power equal or equivalent to the refraction error of the user corresponding to sharp vision at infinite distance. Or it can have an equivalent optical power corresponding to sharp vision at an intermediate distance. This allows to simulate progressive designs varying from intermediate to near vision.

In certain embodiments the first support for supporting the PAL lens is adjustable for setting the position of the progressive addition lens within the PAL plane. For this purpose, the apparatus may comprise some mechanical arrangement for vertically and/or horizontally displacing the first support, such that the PAL lens is displaced vertically and/or horizontally with respect to an optical axis of the projection system PS and the eye of the user. As an alternative or a complement, the first support may be fixed and include in itself means for carrying out the vertical and horizontal displacement of the PAL lens within the PAL plane. Either way, this provides an improved performance of the apparatus since it allows to have an overall wide field of view. Advantageously, an overall field of view of around 100 degrees or more can be achieved, comparable to the field of view of interest in the progressive spectacles.

In certain embodiments the first support for supporting the PAL lens is axially adjustable for setting the position of the PAL plane. This way, the position of the PAL plane can be axially fixed with respect to the projection of the pupil of the user, allowing to modify the first distance.

The vertical, horizontal and axial displacement of the PAL lens can be achieved by means of a single mechanical arrangement, or by separate mechanical arrangements.

In certain embodiments the apparatus further comprises means for adjusting the position of the second support and/or third support such that an axis of the trial lens is coaxial to the optical axis of the projection system, and/or for positioning the trial lens at the conjugated pupil plane generated by the projection system PS.

In certain embodiments the projection system comprises:
a first optical unit comprising a group of lenses and/or mirrors for focusing a collimated or nearly collimated light beam propagated from an object through the PAL plane, at a first intermediate image plane, the first optical unit being placed in a distal end of the projection system;
a second optical unit or relay unit comprising a group of lenses and/or mirrors for generating a conjugate image of the first intermediate image plane, at a second intermediate image plane; and
a third optical unit comprising a group of lenses and/or mirrors for collimating or nearly collimating the light beam from the second intermediate image plane.

This configuration has the advantage that it can result in a compact optical system and that can be easily mounted using, as first and third units, two identical wide field of view optical systems such as eyepieces, the third one reversed with respect to the other.

In certain embodiments the projection system comprises an array of spherical refractive surfaces, and/or two or more mirrors. And/or a set of spherical refractive surfaces in combination with a freeform optical element with at least three refractive and reflective optical surfaces.

In certain embodiments the projection system comprises at least one freeform optical element with at least one refractive or reflective optical surface, in combination or not with an array of spherical refractive surfaces and/or mirrors.

The present disclosure also relates to a binocular apparatus which comprises two apparatuses as defined in the foregoing the apparatuses being placed side by side. Typically, a first apparatus is for a left eye and a second apparatus for a right eye. The two apparatuses are preferably placed in a parallel fashion (or nearly parallel fashion) with respect to each other and at an adjustable distance between them for their alignment with both eyes of the user, in order to match the interpupillary distance of the user.

Another aspect of the invention relates to a method for projecting a progressive addition lens in front of an eye of a user of the apparatus, the method comprising
arranging a progressive addition lens at a PAL plane;
projecting without inversion the PAL plane onto a conjugated PAL plane;
arranging an object in front of the progressive addition lens; and
generating a non-inverted projection of the object through the PAL plane onto a retina of the eye, the eye being located at a vertex distance from the conjugated PAL plane.

Light coming from the object firstly goes through the PAL lens, secondly passes through the projecting system and finally enters the eye Another aspect of the invention relates to the above method carried out by an apparatus as defined in the foregoing.

In certain embodiments the method further comprises moving a field of view of the projecting system across a Far Zone and a Near Zone of the progressive addition lens within the PAL plane.

In the present disclosure, the progressive addition lens can also be an optoadjustable progressive addition lens, for example a programmable PAL lens implemented in a reflective or refractive Spatial Light Modulator or a deformable mirror, or an array of optotunable lenses.

Thus, the apparatus as defined in the foregoing provides a solution that gives the user the possibility of testing and experience different real progressive lenses, thus being able to observe the real environment before actually purchasing their glasses and helping the optometrist to select the most appropriate progressive correction for the user.

The different aspects and embodiments of the invention defined in the foregoing can be combined with one another, as long as they are compatible with each other.

Additional advantages and features of the invention will become apparent from the detailed description that follows and will be particularly pointed out in the appended claims.

BRIEF DESCRIPTION OF THE DRAWINGS

To complete the description and in order to provide for a better understanding of the invention, a set of drawings is provided. Said drawings form an integral part of the description and illustrate embodiments of the invention, which should not be interpreted as restricting the scope of the invention, but just as examples of how the invention can be carried out. The drawings comprise the following figures.

DESCRIPTION OF WAYS OF CARRYING OUT THE INVENTION

The following description is not to be taken in a limiting sense but is given solely for the purpose of describing the broad principles of the invention. Embodiments of the apparatus and method of the present disclosure will be described by way of example, with reference to the accompanying drawings.

Figure 3A:
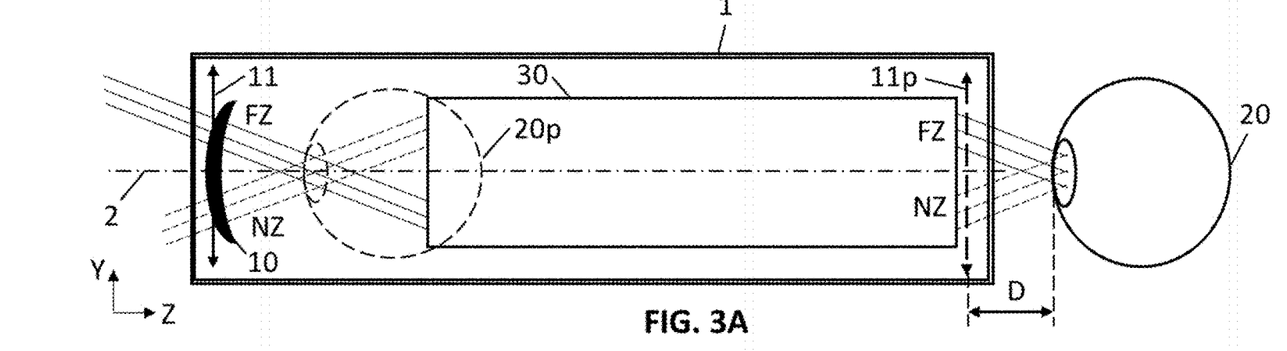
FIG. 3A shows a schematic side view of a possible embodiment of the apparatus proposed herein supporting the PAL lens.
Figure 3B:
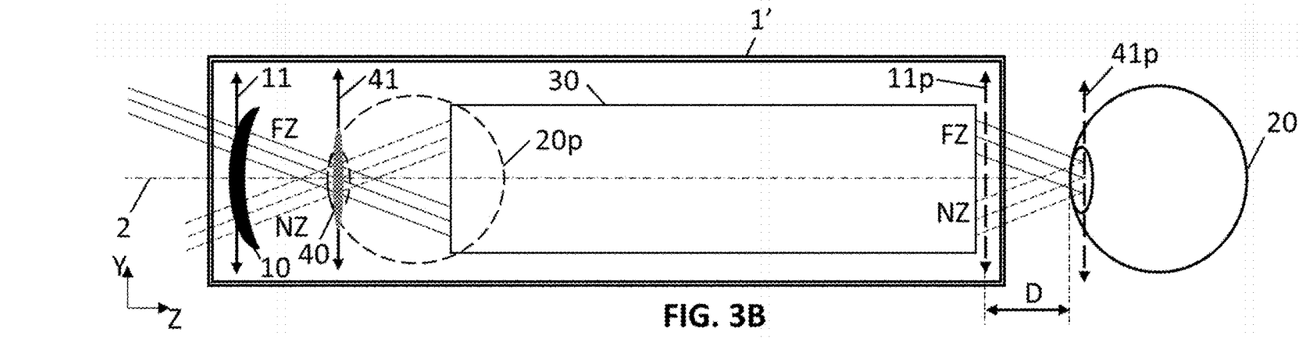
FIG. 3B also shows a schematic side view of another possible embodiment of the apparatus, with the addition of a trial lens.

The present disclosure presents an apparatus for projecting a PAL lens 10 in an eye 20 of a user of the apparatus. Two possible embodiments of this apparatus 1, 1' are schematically represented in FIGS. 3A and 3B from a side view and will be described in the following. Both embodiments of the apparatus 1, 1' shown in FIGS. 3A and 3B are physically embodied as a head-mounted see-through devices which are capable of projecting any blank ophthalmic progressive lens into the user's vision, and in the embodiment of FIG. 3B, together with their refractive error correction. The apparatus 1,1' is a wide field see-through apparatus with a constant magnification factor of ×1 ensuring a natural observance of objects through the project any ophthalmic lens design, and thus being able to simulate the vision through different designs of progressive ophthalmic lenses.

Both apparatuses 1-1' shown in FIGS. 3A-3B, respectively, are based on optical components comprising refractive and reflective surfaces, without the need of any computation station, image processing unit or active optical elements. Either apparatus 1-1' comprises two observation channels, one observation channel for each eye 20 (only one observation channel and one eye 20 are represented in FIGS. 3A-3B, since they represent lateral views of the apparatus). This results in a binocular instrument with a magnification factor of ×1.

Each apparatus 1, 1' (represented by a double line) includes a projection system 30 (also referred to as 'PS' in the present disclosure) and a support (not shown) for supporting a PAL lens 10. This PAL lens 10 is thus supported in the apparatus 1, 1' at a PAL plane 11. In dashed lines, components optically projected through the projection system 30 are depicted such as: the PAL plane 11 is projected to 11p, the trial lens 41 is projected to 41p and the eye 20 is projected to 20p. When the apparatus 1, 1' is in use, usually mounted on the head of the user, the projection system 30 is before the eye 20 of the user, considering the direction of light coming from an external object and going into the eye of the user, and after the support for the PAL lens 10. Thus, in the position of use of the apparatus, the support for the PAL lens 10 (and thus the PAL lens) is placed before the PS 30 and the user's eye 20 is placed after the PS 30. The projection system 30 comprises an optical system including a conventional array of refractive lenses and/or mirrors. Or the optical system of the PS 30 can include a freeform optical component with multiple reflective and refractive surfaces.

In both FIGS. 3A-3B two beams are represented, each beam corresponding to each of the vision zones of the PAL defined previously, the far zone FZ and the near zone NZ. The beam passing through the top of the PAL corresponds to far vision FZ (straight line) while the beam at the bottom corresponds to near vision NZ (dotted line).

The PAL plane 11 is projected without inversion by the projection system 30 onto a conjugated PAL plane 11p at a vertex distance D of the eye 20. The PS 30 generates a non-inverted projection of an object located in front of the PAL lens (typically at a distance of at least 20 cm) through the PAL plane 11 onto the retina of the eye 20.

The apparatus 1, 1' simultaneously projects the conjugated eye 20p at the same vertex distance D as the vertex distance between the conjugated PAL plane 11p and the user's eye 20. This way, the apparatus 1,1' can either be understood as a projector of the user's pupil plane at a vertex distance D with respect to the PAL plane 11.

The apparatus 1' shown in FIG. 3B is similar to the apparatus 1 shown in FIG. 3A. The apparatus 1' further includes another support (also not shown) for supporting at least a trial lens 40 (also referred to as 'TL' in the present disclosure) at a TL plane 41 superimposed with the projected user's pupil plane, for example, at a vertex distance D from the PAL plane 11. This way, trial lenses 40 can be added if needed in the optical path of the apparatus 1' to compensate the user's refractive error (sphere and astigmatism). The support for the trial lenses 40 supports the trial lens 40 between the support for the PAL lens and the projection system 30, at the position of the projected pupil plane. Thus, the apparatus 1' also projects a conjugated TL plane 41p at the pupil plane of the user's eye.

Alternatively, the support for at least one trial lens can also be located in a position where the projected TL plane is not exactly at the pupil plane of the user's eye, but slightly before or after. Furthermore, the support or a third support could also be located just in front of the eye. In any case, trial lenses can be added if needed in the optical path of the apparatus 1' to compensate the user's refractive error (sphere and astigmatism).

For a proper performance of the apparatus, it is important to have an overall wide field of view, of the range of 100 degrees, comparable to the field of view of spectacles, particularly in the vertical direction. To ensure this feature, two possible configurations have been envisaged.

Figure 4:
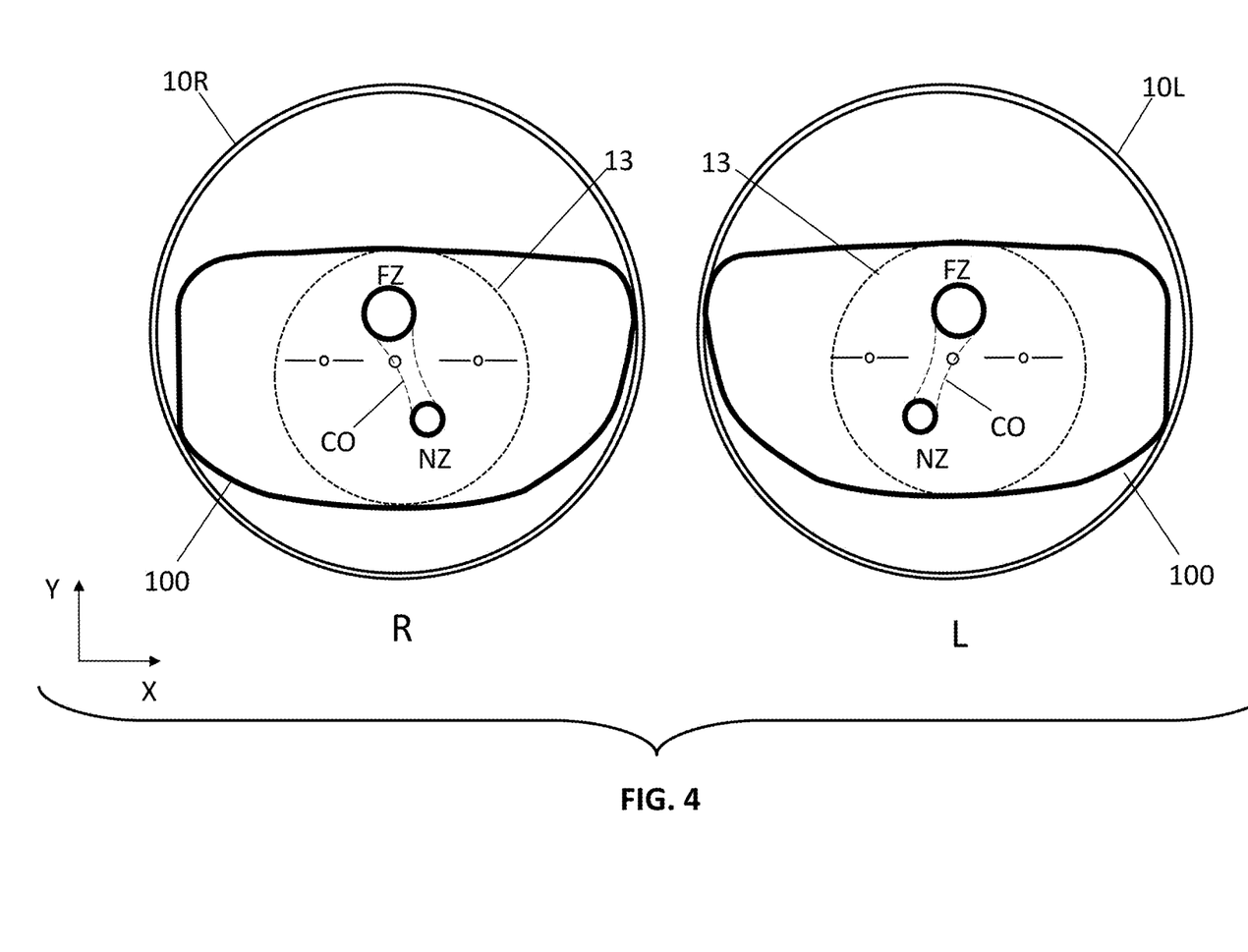
FIG. 4 shows the frontal view of a possible configuration of the apparatus, in which the projection system has a wide field of view 13 covering both the near and the far zones of the PAL lens at the same time.

According to a first configuration, which is shown in FIG. 4, the superposition of the PAL lenses—left PAL lens 10L and right PAL lens 10R—and the field of view 13 (represented by the dotted circles) of the user provides a wide field of view simultaneously covering the complete desired area, including the far zone FZ and the near zone NZ. The spectacles frame 100 is also represented.

Figure 5A:
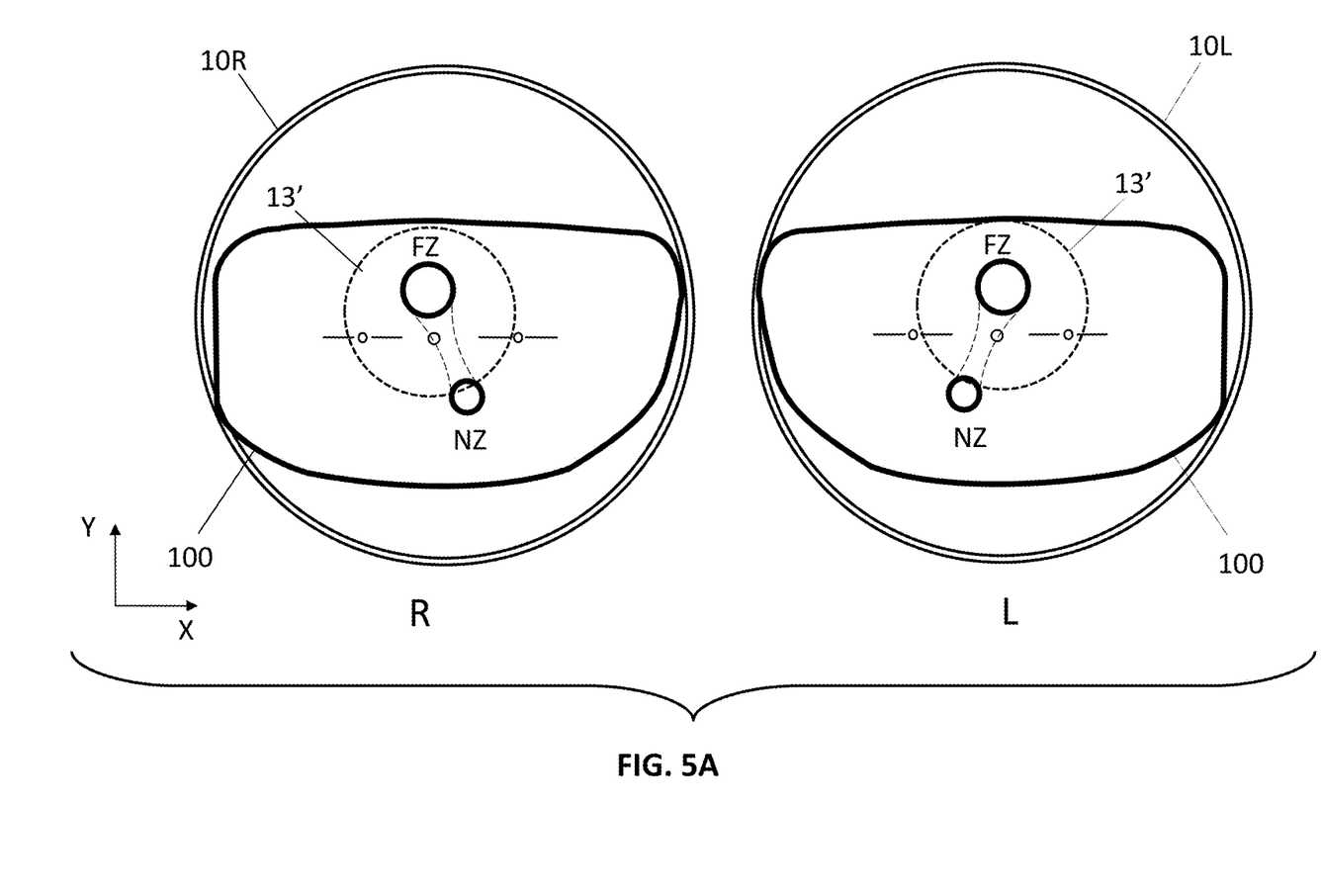
FIGS. 5A and 5B show the frontal view of another possible configuration of the apparatus, with a wide but narrower field of view (13') in which the near and the far zones of the PAL lens are covered by vertically displacing the relative position of the PAL lens with respect to the projection system.
Figure 5B:
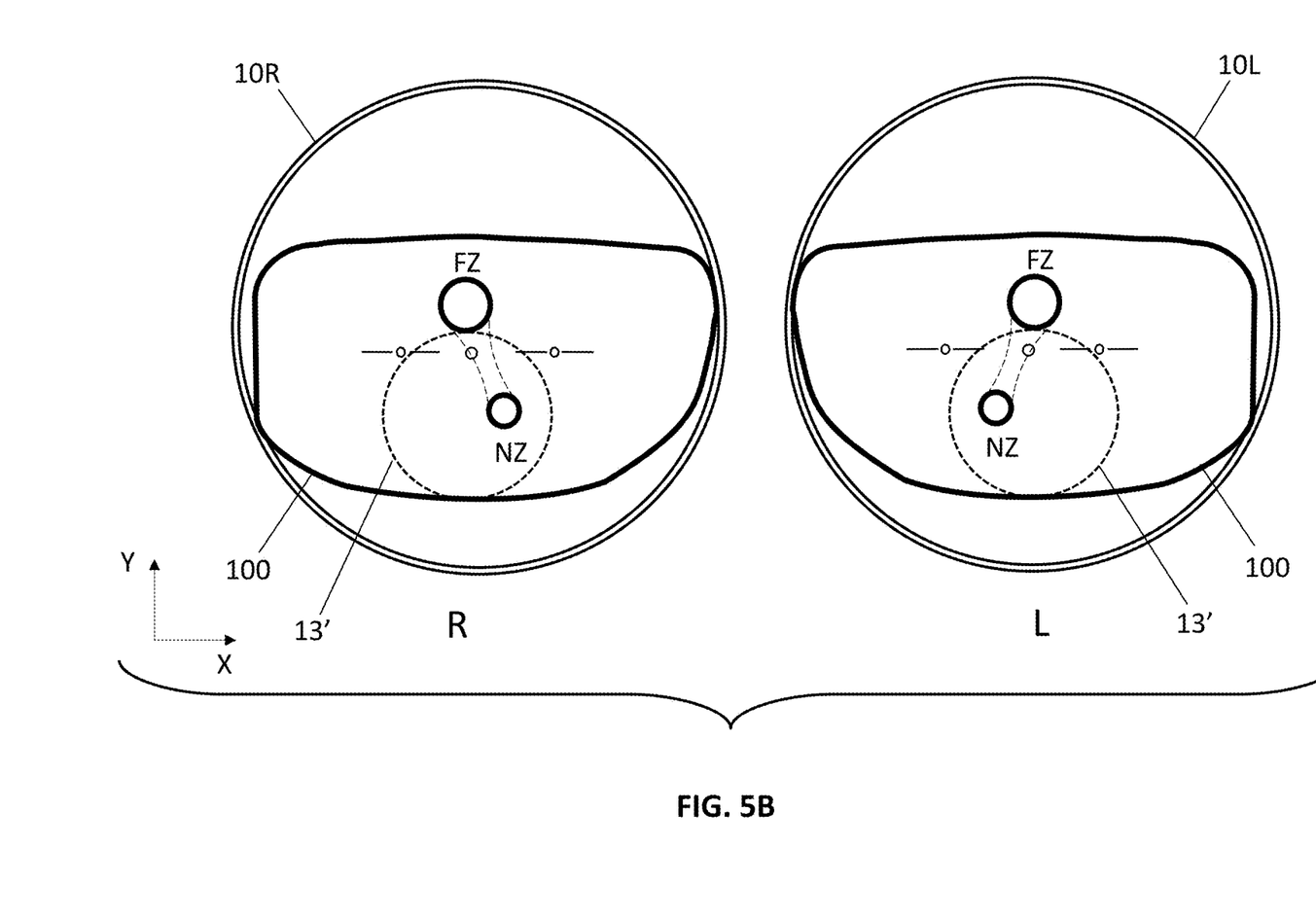

Another possible configuration is schematically shown in FIGS. 5A and 5B, where in a similar way to FIG. 4, the PAL lenses—left and right 10L and 10R—and the spectacle frame 100 are represented. According to this option, a total wide field of view is covered by means of the vertical displacement of the PAL lens 10 with respect to the optical axis of the PS, which in this configuration presents a wide but narrower field of view. In this case, at least two viewing situations are required in order to provide the user with a complete vision experience: first, the field of view 13' (dotted line) is centered at the far zone FZ and covers, at least, a small portion of the near zone NZ, as shown in FIG. 5A; then, the position of the PAL lens 10 is vertically displaced to provide a field of view 13' which is centered at the near zone NZ and covers, at least, a small portion of the far zone FZ as shown in FIG. 5B. For this purpose, the apparatus includes a mechanical arrangement for a fine vertical positioning of the PAL with respect to the projection system.

Figure 6:
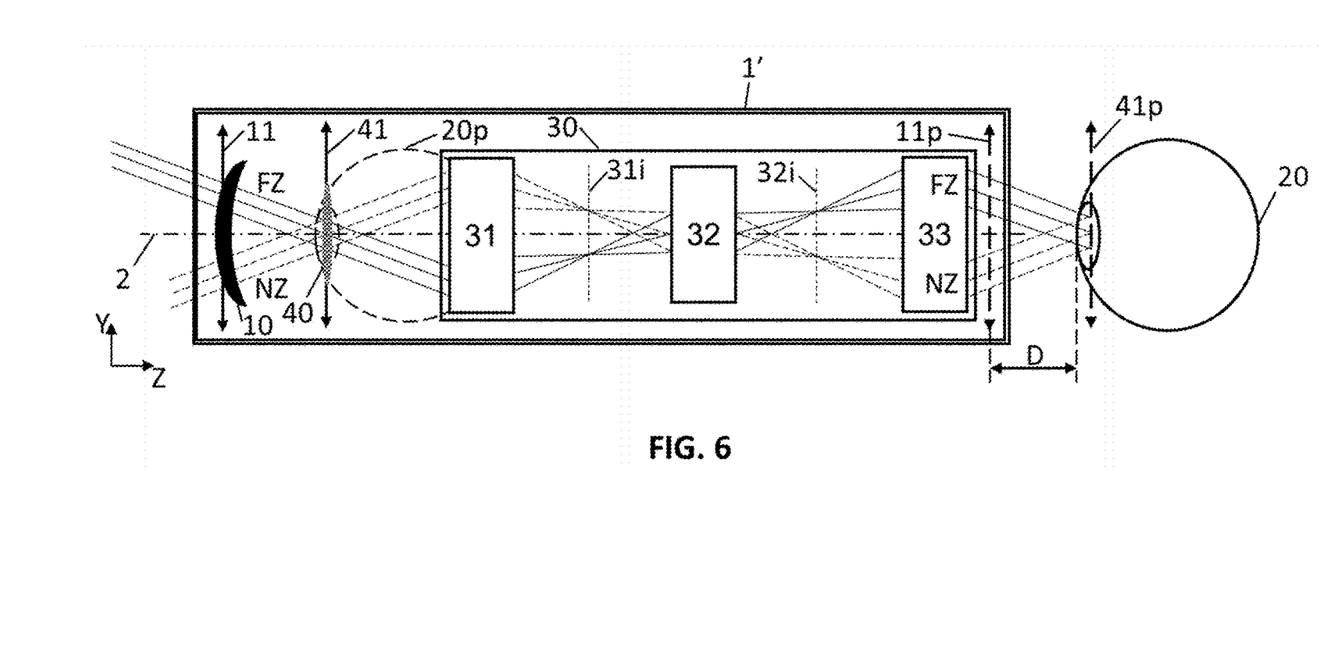
FIG. 6 shows a similar view to that of FIG. 3, with more detail on the projection system showing a block schematic description of it.

FIG. 6 is a similar representation to that of FIG. 3B, showing a side view of the apparatus 1' with support for both a PAL lens 10 and a group of trial lenses 40. This FIG. 6 schematically represents a possible example of the projection system, which is an optical system with three separated optical units:

A first optical unit 31 comprising a group of lenses such as an eyepiece and/or mirrors) that gathers light from a wide field of view. This first eyepiece has a fix magnification factor and an eye relief typically equal or larger to 20 mm. The functionality of this first optical unit is to focus a collimated light beam propagated from an object through the PAL plane 11, at a first intermediate image plane 31i.

A second optical unit or relay unit 32 comprising a group of lenses and/or mirrors for generating a conjugate image of the first intermediate image plane 31i, at a second intermediate image plane 32i for providing a finite conjugate image plane of the focal plane after the first optical unit 31 with a 1:1 imaging ratio. And, A third optical unit 33 comprising a group of lenses such as an eyepiece and/or mirrors for collimating the light beam from the second intermediate image plane 32i.

Thus, a non-inverted image is obtained with a magnification factor of ×1. As in FIGS. 3A and 3B, two beams are represented corresponding to the far zone FZ in the top of the PAL lens 10 and the near zone NZ at the bottom of the PAL lens 10.

Figure 7:
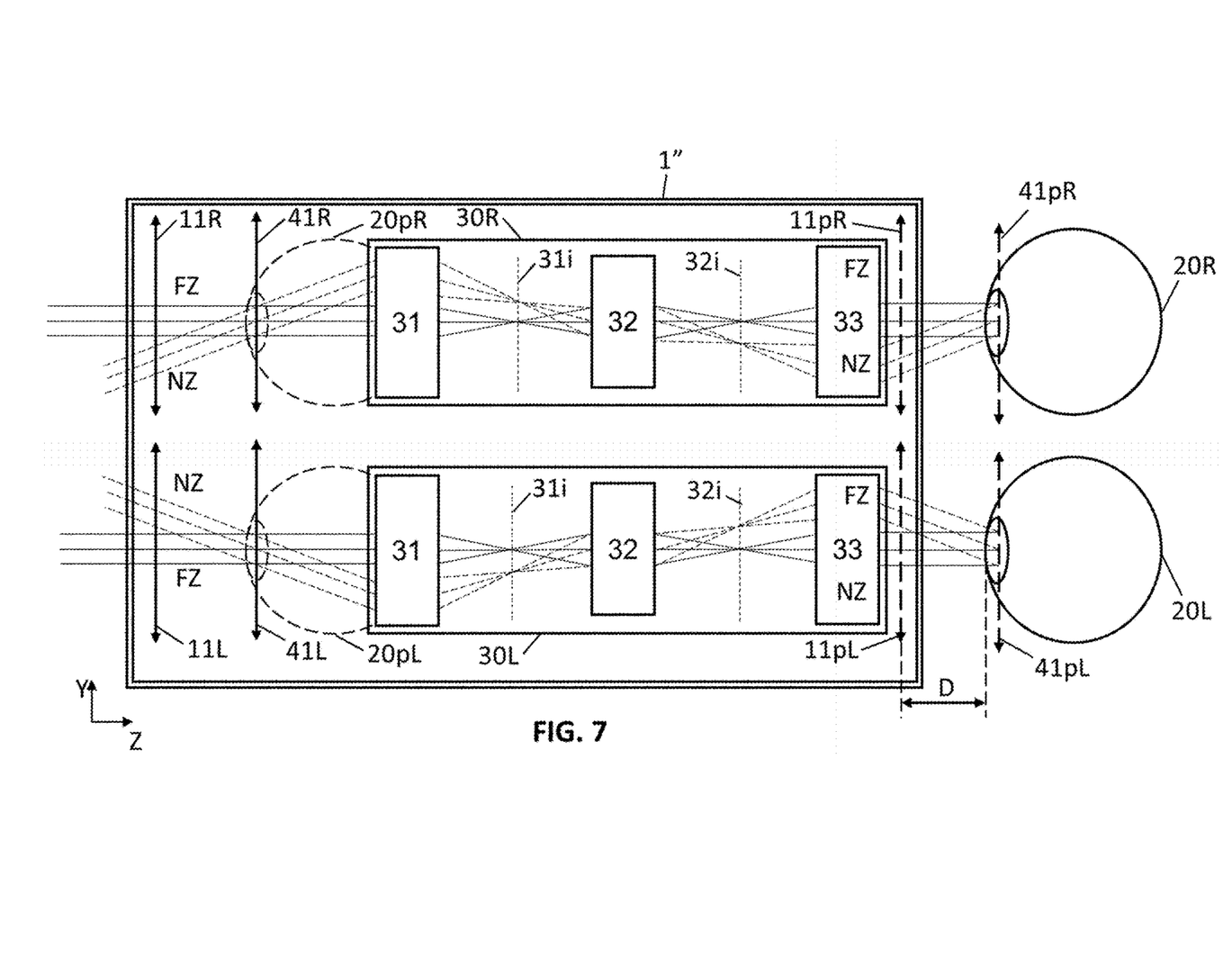
FIG. 7 is a block diagram representation of a top view of a binocular apparatus wherein each channel for each eye involves the apparatus example description shown in FIG. 6.

FIG. 7 is a block diagram of a top view of a binocular apparatus 1". The binocular apparatus 1" comprises two apparatus 1' as described with respect to FIG. 3B, one for the left eye 20L and one for the right eye 20R. The same reference numbers as in FIG. 3B are used in this representation, with the addition of the letters L, R for the left and right cases, respectively.

As in previous figures, two beams are represented for each apparatus 1', one corresponding to the far zone FZ, which beam passes centered at the optical axis of the apparatus, and another beam corresponding to the near zone NZ, which beam is tilted with respect to the optical axis of the apparatus due to the eye convergence at near vision.

Figure 8:
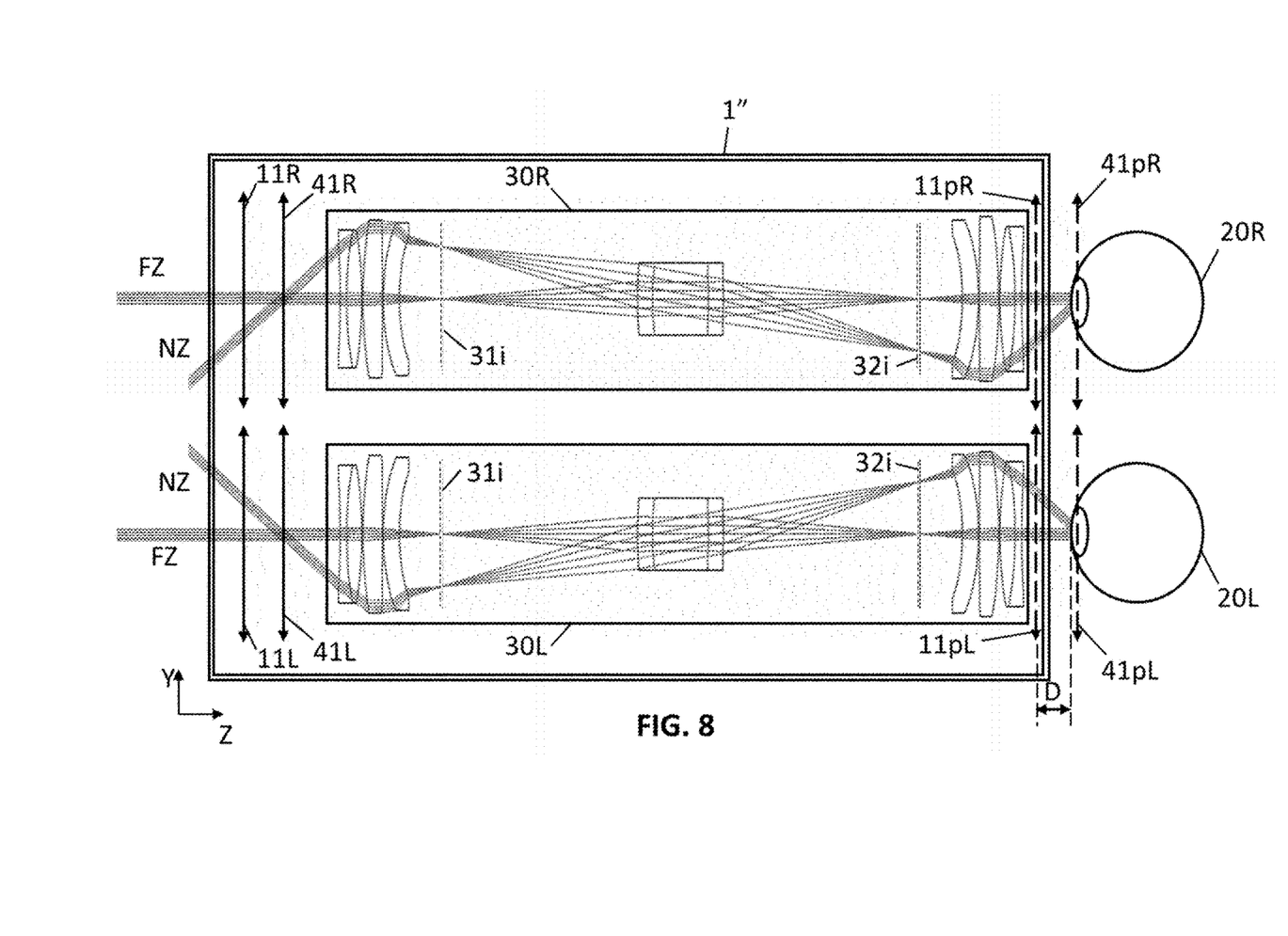
FIG. 8 also shows a top view of a binocular apparatus, showing an example detailed description of the physical elements of the projection system.

In FIG. 8 the physical components of elements of the projection systems are shown: the first optical unit 31, the second optical unit or relay unit 32 and the third optical unit 33 comprise a set of spherical refractive surfaces and/or mirrors. Additionally, the projection system 30 includes mirrors 34 to fold the optical path of the beams to reduce the overall length of the apparatus. The same reference numbers as in FIG. 3B are used in this representation, with the addition of the letters L, R for the left and right cases, respectively.

Abbreviations and acronyms used in the present disclosure:
AR: Augmented Reality
FZ: Far Zone of the PAL
IOL: Intraocular Lenses
NZ: Near Zone of the PAL
PAL: Progressive Addition lenses
PS: Projection System
TL: Trial Lens
VR: Virtual Reality In this text, the terms first, second, third, etc. have been used herein to describe several devices, elements or parameters, it will be understood that the devices, elements or parameters should not be limited by these terms since the terms are only used to distinguish one device, element or parameter from another. For example, the first support could as well be named second support and vice versa, without departing from the scope of this disclosure.

In this text, the term "comprises" and its derivations (such as "comprising", etc.) should not be understood in an excluding sense, that is, these terms should not be interpreted as excluding the possibility that what is described and defined may include further elements, steps, etc.

On the other hand, the invention is obviously not limited to the specific embodiment(s) described herein, but also encompasses any variations that may be considered by any person skilled in the art (for example, as regards the choice of materials, dimensions, components, configuration, etc.), within the general scope of the invention as defined in the claims.

The invention claimed is:

1. An apparatus for projecting a progressive addition lens in front of an eye of a user of the apparatus, the apparatus comprising:
a first support for supporting the progressive addition lens in a PAL plane;
a projection system configured for:
projecting without inversion the PAL plane onto a conjugated PAL plane, and
generating a non-inverted projection of an object through the PAL plane onto a retina of the eye;
wherein in the position of use of the apparatus:
the first support is configured to support the PAL lens such that the PAL plane is placed in a distal portion of the apparatus;
the projection system is located between the PAL plane and the eye;
a proximal portion of the apparatus is to be placed in front of the eye, and
the eye is placed at a first distance from the conjugated PAL plane.

2. The apparatus of claim 1, wherein the first support is adjustable for setting the position of the progressive addition lens within the PAL plane.

3. The apparatus of claim 1, wherein the first support is adjustable for setting the position of the PAL plane.

4. The apparatus of claim 1, further comprising a second support for supporting at least one trial lens in a first trial lens plane, the second support being configured to support the at least one trial lens in front of the eye, at a second distance therefrom.

5. The apparatus of claim 4, wherein the at least one trial lens to be supported by the second support or by the third support has an optical power equal to the refraction error of the user corresponding to sharp vision at infinite distance.

6. The apparatus of claim 4, wherein the at least one trial lens to be supported by the second or by the third supports has an optical power corresponding to sharp vision at an intermediate distance.

7. The apparatus of claim 1, further comprising a third support for supporting at least one trial lens in a second lens plane, the second lens plane being configured to be projected at a conjugated trial lens plane at the pupil of the eye or at a second distance from the eye.

8. The apparatus of claim 7, wherein the at least one trial lens to be supported by the second support or by the third support has an optical power equal to the refraction error of the user corresponding to sharp vision at infinite distance.

9. The apparatus of claim 7, wherein the at least one trial lens to be supported by the second or by the third supports has an optical power corresponding to sharp vision at an intermediate distance.

10. The apparatus of claim 1, wherein the projection system comprises:
a first optical unit comprising a group of lenses or mirrors for focusing a collimated or nearly collimated light beam propagated from an object through the PAL plane, at a first intermediate image plane, the first optical unit being placed in a distal end of the projection system;
a second optical unit or relay unit comprising a group of lenses or mirrors for generating a conjugate image of the first intermediate image plane, at a second intermediate image plane;
a third optical unit comprising a group of lenses or mirrors for collimating or nearly collimating the light beam from the second intermediate image plane.

11. The apparatus of claim 1, wherein the projection system is at least one freeform optical element with at least one refractive or reflective optical surface, in combination or not with an array of spherical refractive surfaces or mirrors.

12. A binocular apparatus comprising:
a first apparatus for projecting a first progressive addition lens in front of an eye of a user of the apparatus and a second apparatus for projecting a second progressive addition lens in front of an eye of a user of the apparatus, the first apparatus being placed side by side with the second apparatus;
the first apparatus and the second apparatus, each comprising:
a first support for supporting the progressive addition lens in a PAL plane;
a projection system configured for:
projecting without inversion the PAL plane onto a conjugated PAL plane, and
generating a non-inverted projection of an object through the PAL plane onto a retina of the eye;
wherein in the position of use of the respective apparatus:
the first support is configured to support the PAL lens such that the PAL plane is placed in a distal portion of the apparatus;
the projection system is located between the PAL plane and the eye;
a proximal portion of the apparatus is to be placed in front of the eye, and
the eye is placed at a first distance from the conjugated PAL plane.

13. The binocular apparatus of claim 12, wherein the first apparatus and the second apparatus are disposed parallelly or nearly parallelly with respect to each other and at an adjustable distance between them for their alignment with both eyes of the user.

14. A method for projecting a progressive addition lens in front of an eye of a user of the apparatus, the method comprising the steps of:
arranging a progressive addition lens at a PAL plane;
projecting without inversion the PAL plane onto a conjugated PAL plane;
arranging an object in front of the progressive addition lens; and
generating a non-inverted projection of the object through the PAL plane onto a retina of the eye, the eye being located at a vertex distance from the conjugated PAL plane.

15. The method of claim 14, carried out by an apparatus for projecting a progressive addition lens in front of an eye of a user of the apparatus, the apparatus comprising:
a first support for supporting the progressive addition lens in a PAL plane;
a projection system configured for:
projecting without inversion the PAL plane onto a conjugated PAL plane;
generating a non-inverted projection of an object through the PAL plane onto a retina of the eye;
wherein in the position of use of the apparatus:
placed in a distal portion of the apparatus;
the projection system is located between the PAL plane and the eye;
a proximal portion of the apparatus is to be placed in front of the eye, and
the eye is placed at a first distance from the conjugated PAL plane.

16. The method of claim 15, which further comprises moving a field of view of the projecting system across a Far Zone and a Near Zone of the progressive addition lens within the PAL plane.

17. The method of claim 14, wherein the progressive addition lens is an optoadjustable progressive addition lens.

* * * * *